United States Patent
Basheer et al.

(10) Patent No.: US 10,405,069 B2
(45) Date of Patent: Sep. 3, 2019

(54) MODULAR SENSOR ARCHITECTURE FOR SOIL AND WATER ANALYSIS AT VARIOUS DEPTHS FROM THE SURFACE

(71) Applicant: urban-gro, Inc., Lafayette, CO (US)

(72) Inventors: Mohammed Rana Basheer, Costa Mesa, CA (US); Atul A. Patel, Irvine, CA (US)

(73) Assignee: urban-gro, Inc., Lafayette, CO (US)

( * ) Notice: Subject to any disclaimer, the term of this patent is extended or adjusted under 35 U.S.C. 154(b) by 10 days.

(21) Appl. No.: 15/626,079

(22) Filed: Jun. 17, 2017

(65) Prior Publication Data

US 2017/0366877 A1   Dec. 21, 2017

Related U.S. Application Data

(60) Provisional application No. 62/351,989, filed on Jun. 19, 2016.

(51) Int. Cl.

| | |
|---|---|
| *G01N 33/24* | (2006.01) |
| *G01N 33/18* | (2006.01) |
| *G01D 18/00* | (2006.01) |
| *G01D 21/00* | (2006.01) |
| *G06F 9/4401* | (2018.01) |
| *H04Q 9/00* | (2006.01) |
| *G06F 1/26* | (2006.01) |
| *G06F 13/40* | (2006.01) |

(52) U.S. Cl.
CPC ............ *H04Q 9/00* (2013.01); *G01D 18/00* (2013.01); *G01D 21/00* (2013.01); *G01N 33/18* (2013.01); *G01N 33/24* (2013.01); *G06F 1/26* (2013.01); *G06F 9/4418* (2013.01); *G06F 13/4086* (2013.01); *H04Q 2209/10* (2013.01); *H04Q 2209/40* (2013.01); *H04Q 2209/82* (2013.01); *H04Q 2209/886* (2013.01); *Y02D 10/14* (2018.01); *Y02D 10/151* (2018.01)

(58) Field of Classification Search
None
See application file for complete search history.

(56) References Cited

U.S. PATENT DOCUMENTS

| | | | | |
|---|---|---|---|---|
| 4,492,111 A | * | 1/1985 | Kirkland | G01N 3/48 324/323 |
| 4,567,563 A | * | 1/1986 | Hirsch | A01G 25/16 700/284 |
| 4,852,054 A | * | 7/1989 | Mastandrea | G01F 23/0076 340/605 |
| 6,119,535 A | * | 9/2000 | Tambo | G08B 21/10 73/865.8 |

(Continued)

FOREIGN PATENT DOCUMENTS

WO   WO-2015038991 A1 * 3/2015 ............. G01C 23/00

*Primary Examiner* — Steven Lim
*Assistant Examiner* — Muhammad Adnan
(74) *Attorney, Agent, or Firm* — Polsinelli PC

(57) ABSTRACT

A modular sensor system may perform soil and water analysis at various depths. For instance, chemical composition may be determined and concentration and/or environmental parameters, such as pressure, temperature, and/or moisture, may be measured at different depths. A sensor bus head, at least one sensor rod, and a sensor bus terminus may be vertically stacked and interconnected through a bus network such that the system is modular and reconfigurable.

14 Claims, 5 Drawing Sheets

(56) References Cited

U.S. PATENT DOCUMENTS

| | | | | |
|---|---|---|---|---|
| 6,317,694 B1* | 11/2001 | Kram | B09C 1/00 | 702/11 |
| 6,647,799 B1* | 11/2003 | Raper | E02D 1/022 | 73/73 |
| 6,975,236 B2* | 12/2005 | Staples | A01G 25/167 | 340/602 |
| 6,975,245 B1* | 12/2005 | Slater | A01G 25/167 | 340/870.16 |
| 7,183,779 B2* | 2/2007 | Hughes | G01N 33/246 | 324/664 |
| 7,311,011 B2* | 12/2007 | Clark | E02D 1/06 | 73/864.74 |
| 7,705,616 B2* | 4/2010 | Hawkins | G01N 33/246 | 324/696 |
| 7,788,970 B2* | 9/2010 | Hitt | A01G 25/167 | 73/73 |
| 8,058,885 B2* | 11/2011 | Caron | G01V 3/06 | 324/453 |
| 8,981,946 B2* | 3/2015 | Runge | A01G 25/167 | 137/78.2 |
| 9,411,070 B2* | 8/2016 | Chang | G01V 9/00 | |
| 9,605,404 B2* | 3/2017 | Hale | E02D 33/00 | |
| 9,606,087 B1* | 3/2017 | Taylor | G01N 29/04 | |
| 2003/0066357 A1* | 4/2003 | Upadhyaya | A01B 79/005 | 73/818 |
| 2003/0074505 A1* | 4/2003 | Andreas | G06F 13/4256 | 710/110 |
| 2003/0219062 A1* | 11/2003 | Egidio | G01K 1/026 | 374/170 |
| 2003/0233885 A1* | 12/2003 | Bird | G01F 1/115 | 73/861 |
| 2004/0200900 A1* | 10/2004 | Hall | G05B 19/00 | 235/400 |
| 2005/0157843 A1* | 7/2005 | Chen | G01N 23/223 | 378/47 |
| 2005/0196111 A1* | 9/2005 | Burdick | G01M 11/00 | 385/92 |
| 2006/0030971 A1* | 2/2006 | Nelson | A01G 25/165 | 700/284 |
| 2007/0069115 A1* | 3/2007 | Huang | G01B 11/18 | 250/227.14 |
| 2008/0129495 A1* | 6/2008 | Hitt | A01G 25/167 | 340/539.26 |
| 2008/0184827 A1* | 8/2008 | Susfalk | G01D 9/005 | 73/866.5 |
| 2009/0272205 A1* | 11/2009 | Brown | G01L 19/0015 | 73/866.5 |
| 2015/0168594 A1* | 6/2015 | Chang | G01V 9/00 | 73/866 |
| 2015/0335288 A1* | 11/2015 | Toth | A61B 5/6833 | 600/373 |
| 2015/0355152 A1* | 12/2015 | Christian | G01W 1/14 | 702/2 |
| 2015/0379854 A1* | 12/2015 | Kors | G08B 21/182 | 340/618 |
| 2017/0254766 A1* | 9/2017 | Bermudez Rodriguez | G01N 27/048 | |
| 2017/0363451 A1 | 12/2017 | Basheer et al. | | |
| 2018/0156770 A1* | 6/2018 | Saez | B64C 39/02 | |

* cited by examiner

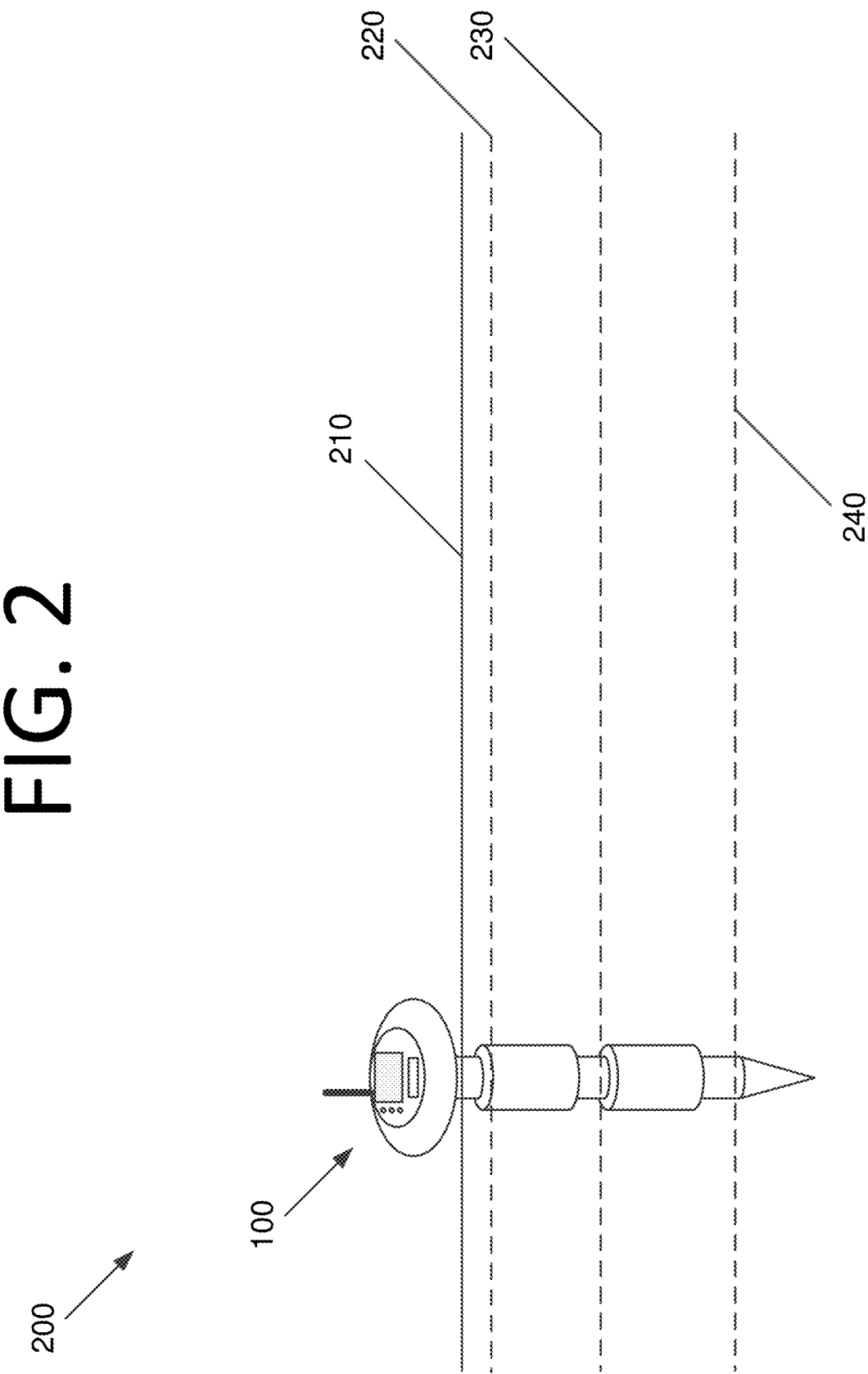

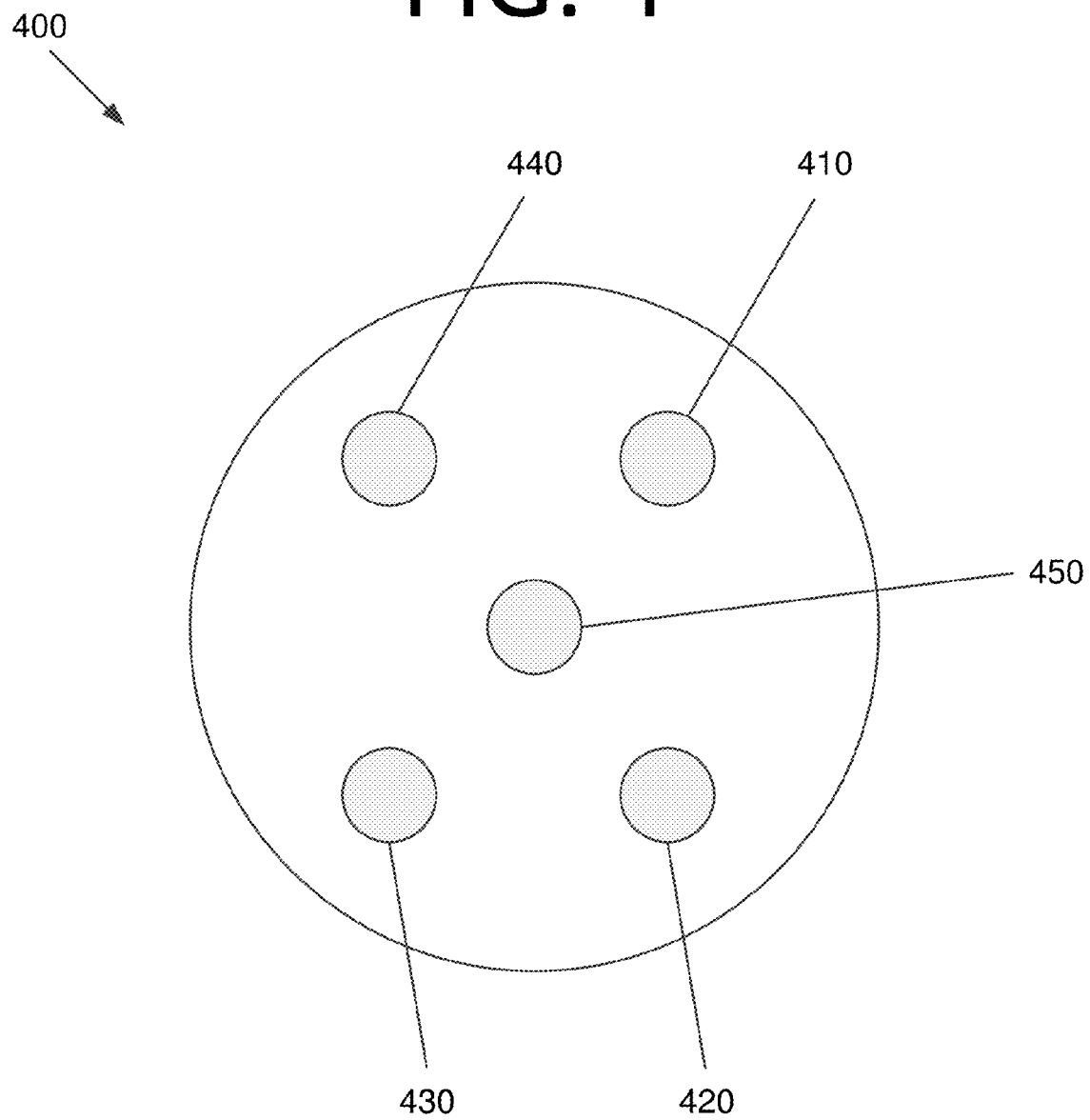

MODULAR SENSOR ARCHITECTURE FOR SOIL AND WATER ANALYSIS AT VARIOUS DEPTHS FROM THE SURFACE

CROSS-REFERENCE TO RELATED APPLICATIONS

This application claims the benefit of U.S. Provisional Patent Application No. 62/351,989 filed Jun. 19, 2016. The subject matter of this earlier filed application is hereby incorporated by reference in its entirety.

FIELD

The present invention generally pertains to soil and water analysis, and more specifically, to a modular sensor architecture for soil and water analysis at various depths from the surface.

BACKGROUND

Soil and water analysis for research, advisory services, formulation of recommendations, and designing appropriate soil management and water management practices is employed for various applications. Soil and water analysis may be conducted for estimating the availability of plant nutrients, geotechnical and ecological investigations, analyzing chemical composition of soil, determining soil moisture content, and measurement of various parameters in water bodies (e.g., pH, dissolved oxygen, oxidation-reduction potential, conductivity or salinity, temperature, turbidity, and dissolved ions such as fluoride, carbide, nitrates, lead, iodine, etc.)

Soil study is often conducted for analyzing soil composition for agronomic purposes. For many years, soil analysis has been used as an aid in assessing soil fertility and plant nutrient management. The soil analysis reports may provide information to set nutrient application targets, which are used to calculate manure and fertilizer application rates. Regular analysis from field sampling allows monitoring and detection of changes in the soil parameters over time, such as nutrients, pH, and salinity. Soil testing, in particular, is also important in monitoring the various types of land degradation and the choice of measures for land improvement. Development of effective and efficient analytical services of soil, water, plant, and fertilizers is thus important for increasing and sustaining land productivity, as well as crop and food production.

A variety of sensors, such as electromagnetic, optical, mechanical, electrochemical, airflow, and acoustic sensors, are conventionally available that can measure various parameters in soil and water. For instance, soil moisture sensors measure the volumetric water content in soil. Certain sensor probes measure temperature, pH, and electrical conductivity. Metal probes may measure the concentration of various elements, such as nitrogen, phosphorous, potassium, etc., in the soil and water.

Since one sensor can typically measure only one parameter, it is difficult to measure more than a single parameter at a time. Moreover, if two or more sensors are used to measure two different parameters, the quantity of the parameters at different levels cannot be ascertained. Accordingly, an improved sensor architecture and device that can analyze different parameters at varying depth may be beneficial.

SUMMARY

Certain embodiments of the present invention may provide solutions to the problems and needs in the art that have not yet been fully identified, appreciated, or solved by conventional soil and water sensor technologies. For example, some embodiments of the present invention pertain to a sensor architecture for soil and water analysis at various depths.

In an embodiment, a modular sensor system includes a sensor bus head located at a top of the modular sensor system and a sensor bus terminus located at the bottom of the modular sensor system. The modular sensor system also includes at least one sensor rod connected between the sensor bus head and the sensor bus terminus. The at least one sensor rod is configured to determine environmental parameters of soil, water, or both, at its respective depth.

In another embodiment, a modular sensor system includes a sensor bus head configured to be located at a top of the modular sensor system. The sensor bus head includes a power and control interface configured to enable a user to select a function of the modular sensor system. The modular sensor system also includes a sensor bus terminus configured to be located at the bottom of the modular sensor system. The modular sensor system further includes at least one sensor rod configured to be connected between the sensor bus head and the sensor bus terminus. The at least one sensor rod is configured to determine environmental parameters of soil, water, or both, at its respective depth.

In yet another embodiment, a system includes a sensor bus head configured to be located at a top of the modular sensor system and a sensor rod configured to be connected with the sensor bus head and another sensor rod. The sensor rod is configured to determine environmental parameters of soil, water, or both, at its respective depth.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 2 illustrates the modular soil and water analysis device deployed in an environment, according to an embodiment of the present invention.

FIG. 4 is a top view illustrating sensor rod connectors, according to an embodiment of the present invention.

DETAILED DESCRIPTION OF THE EMBODIMENTS

Figure 1A:
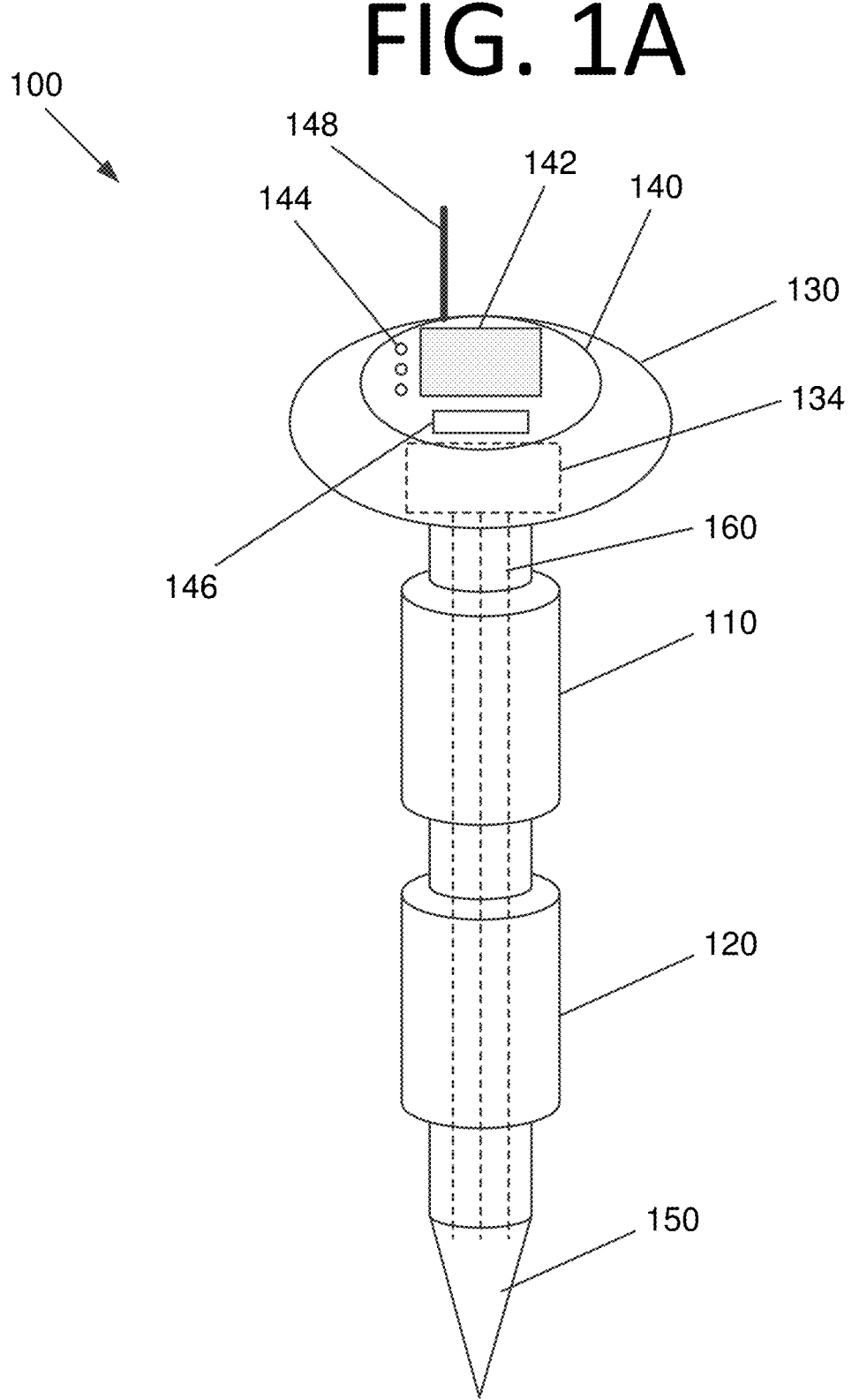
FIG. 1A is a perspective view illustrating a modular soil and water analysis device configured to perform soil and water analysis at different depths, according to an embodiment of the present invention.

Some embodiments of the present invention pertain to a sensor architecture for soil and water analysis at various depths. The system of some embodiments determines chemical composition and measures concentration and/or environmental parameters, such as pressure, temperature, and/or moisture, at different depths. The system of some embodiments has a vertically stacked arrangement of a plurality of sensors interconnected through a bus network. Each of the sensors may be embedded in a rod with input and output connectivity. The sensor rod may be connected to other sensor rods, forming the vertically stacked arrangement. The uppermost sensor rod in the vertically stacked system may be connected to a sensor bus head, and the lowermost sensor rod may be connected to a sensor bus terminus. Between the sensor bus head and the sensor bus terminus, various sensor rods can be connected. Each sensor rod may measure one or more specific parameters. The sensor(s) present in the sensor rod may be chemical composition analyzers, such as sensors for determining concentration of various elements, such as sodium, potassium, phosphorous, calcium, magnesium, sulfur, carbon, and/or other micro-nutrients or macro-nutrients. Additionally or alternatively, the sensors in the sensor rod may measure various environmental and/or chemical parameters, such as temperature, moisture, humidity, pH, pressure, electrical conductivity, salinity, turbidity, acidity, etc.

The system of some embodiments may be used to monitor and analyze soil and/or water. For measuring different parameters, different sensors embedded in different sensor rods may be interconnected between the sensor bus head at the top and the sensor bus terminus at the bottom. The system may then be inserted into the ground or placed in a body of water. In some embodiments that may operate in water, the sensor bus head may be buoyant enough such that the sensor bus head, sensor rod(s), and sensor bus terminus do not sink, and the sensor bus head floats at the surface (e.g., due to air-filled cavities, foam pockets, aerogel pockets, etc.). However, in certain embodiments, the sensor bus head, sensor rod(s) and sensor bus terminus may not be buoyant, and may be deployed in sediment at the bottom of a lake, river, or ocean, for instance. The sensors present at different depths in some embodiments sense the respective parameters for which they are designed and communicate the test results and the specific depth of the sensor to the sensor bus head. The results can then be used for further research and analysis of the soil and/or water.

The modular vertically stacked arrangement of the sensors in the system of some embodiments is provided such that the sensors are interconnected through a sensor bus network. The system may automatically detect the depth at which a particular sensor is positioned in the vertically stacked arrangement. Alternatively, the system may know the size of the rod, and the location of the sensor(s) thereon, and determine the location of the sensor(s) in that manner. The sensor bus communication scheme may allow hot-swapping of sensors and relatively low power operation for energy-constrained sensor data collection applications.

FIG. 1A is a perspective view illustrating a modular soil and water analysis device 100 configured to perform soil and water analysis at different depths, according to an embodiment of the present invention. In this embodiment, device 100 includes two sensor rods 110, 120 that are vertically connected to one another. Sensor rod 110 is connected to sensor bus head 130 at an upper end thereof. Sensor rod 120 is connected to a sensor bus terminus 150 at the lower end thereof. Sensor bus terminus 150 helps to provide water resistance to the terminal of the bus, and in addition, provides the loading to identify the end of the sensor stack.

Sensor bus head 130 includes processing and control circuitry 134 (e.g., a microcontroller, transceiver, etc.) that facilitates operations of sensor bus head 130. Sensor bus head 130 also includes a power and control interface 140 in this embodiment. Power and control interface 140 includes a solar panel 142 to provide power to device 100, controls 144, and a display 146 for displaying various information to the user. For instance, controls 144 and display 146 may enable a user to select a function associated with device 100. Device 100 may be designed to enable analysis of soil and/or water at different depths. Results of the analysis may be provided on display 146. In certain embodiments, sensor bus head 130 may communicate analysis results to a central server using an antenna 148 that allows communication with other modular soil and water analysis devices, a cellular network, local area network (LAN), wide area network (WAN), satellite communications network, or any combination thereof, for instance. In certain embodiments, sensors of sensor rods 110, 120 may communicate their depth to sensor bus head 130. An interconnected bus network 160 runs between, and interconnects, the components of device 100.

Figure 1B:
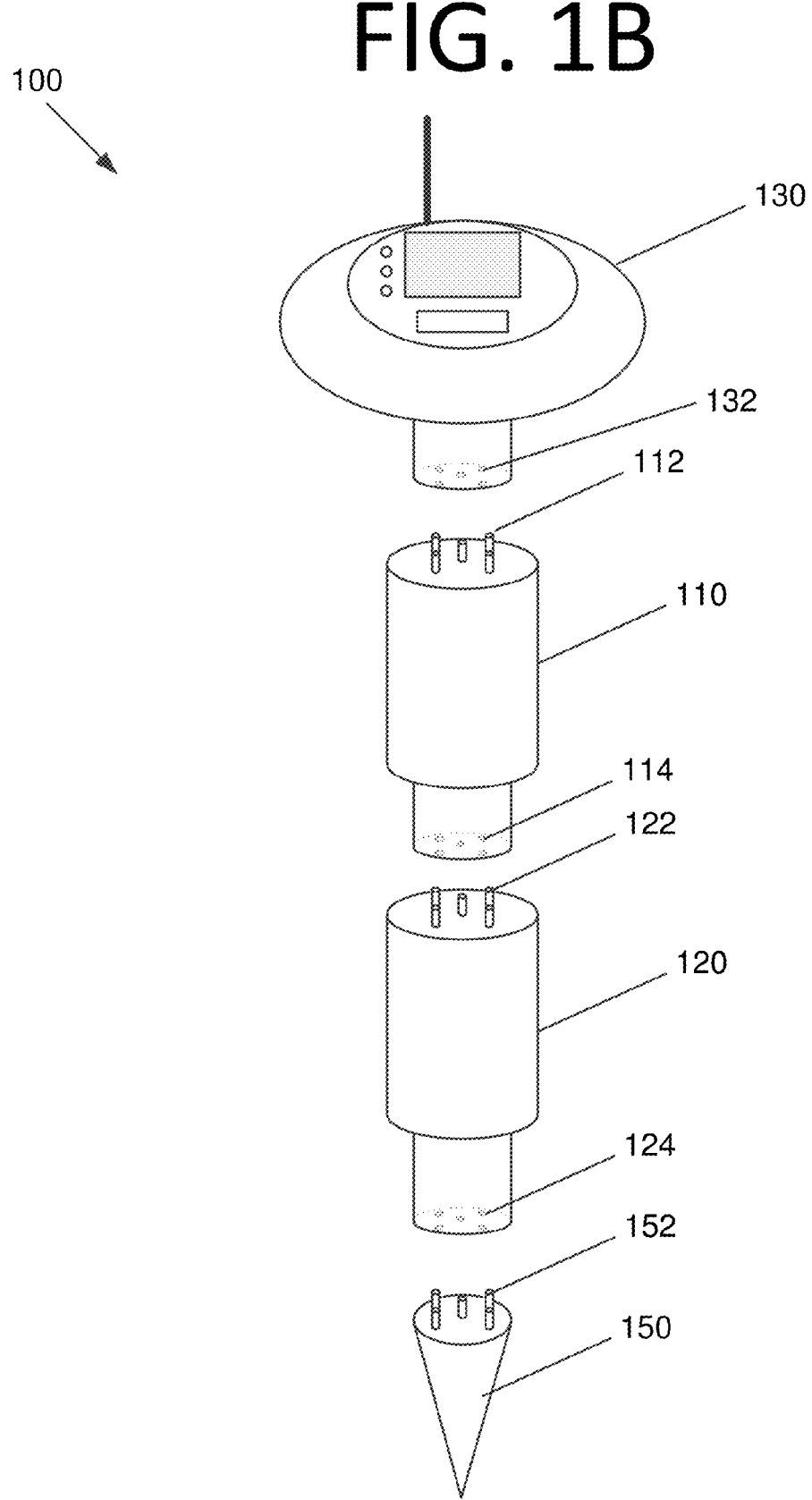
FIG. 1B is a perspective view illustrating disconnected components of the modular soil and water analysis device of FIG. 1A, according to an embodiment of the present invention.

FIG. 1B shows components of device 100 in a disconnected state. In this embodiment, sensor 110 connects to sensor bus head 130, sensor 120 connects to sensor 110, and sensor bus terminus connects to sensor 120 via male connectors 112, 122, 152, respectively (e.g., 5-pin waterproof male connectors), and female connectors 132, 114, 124, respectively (e.g., 5-pin female connectors). Alternatively, the male/female connectors may be reversed among the components (i.e., the female connectors may be on the top and the male connectors may be on the bottom), or some male connectors and some female connectors may be included on both the top and the bottom. Indeed, any suitable connectors and/or connection mechanism may be used to facilitate communication between the various components in other embodiments without deviating from the scope of the invention. As used herein, "pin" may be a port, a pin, or any other suitable connector without deviating from the scope of the invention.

FIG. 2 illustrates modular soil and water analysis device 100 in a deployed environment 200, according to an embodiment of the present invention. Device 100 is deployed in ground or water 210. Sensor rod 110 is located at a depth between layer 220 and 230, whereas sensor rod 220 is located at a depth between layer 230 and 240. Sensor bus head 130 is above ground or water 210, and sensor bus terminus 150 is present below layer 240. The sensor(s) of first sensor rod 110 measure their respective parameters and communicate these parameters to sensor bus head 130. Sensor rod 110 sends the data from its analysis along with an indication the depth at which it is located. Similarly, sensor rod 120 communicates the sensor results, along with the depth at which its analysis is performed, to sensor bus head 130.

Figure 3:
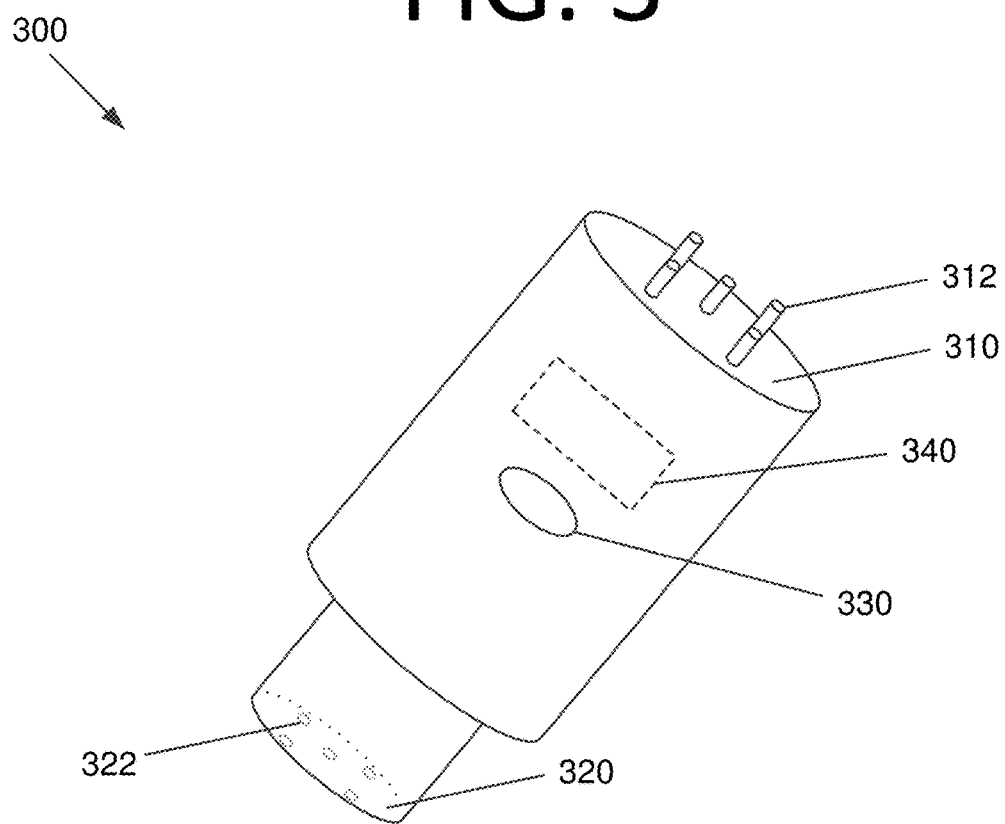
FIG. 3 is a perspective view illustrating a sensor rod, according to an embodiment of the present invention.

FIG. 3 is a perspective view illustrating a sensor rod 300, according to an embodiment of the present invention. Sensor rod 300 includes an upper section 310 including male connectors 312 and a lower section 320 including female connectors. Sensor rod 300 also includes a sensor 330 configured to measure a parameter (or multiple parameters). For instance, in some embodiments, sensor 330 may be an electrode used to measure analyte concentration. A microcontroller 340 is programmed to perform the various functions associated with sensor rod 300 and to communicate with a sensor bus head and a sensor bus terminus.

FIG. 4 is a top view illustrating connectors of a sensor rod 400, according to an embodiment of the present invention. Connector (e.g., pin) 410 is a power (Vcc) pin, where the sensor head will provide supply voltage to connector 410 when it is communicating with sensor rod 400, or other interconnected sensor rods. Connector 410 is shared by all the sensor rods present in the device in this embodiment. To save power, the sensor bus head may turn off the supply voltage when possible without interfering with sensor operations. Connector 420 is a ground (Gnd) pin, which is the reference ground for the entire system in this embodiment. Connector 420 may be shared by all sensor rods in the device. Connector 430 is a data pin that facilitates bidirectional communication between the sensor rods and the sensor bus head. Connector 440 is a clock (CLK) pin that is shared by all stacked sensor rods and is controlled by the sensor bus head. Connector 440 signals the rate at which information is clocked in and out of the sensor rods. Connector 450 is a sensor select SS pin (in/out) and is not shared by all stacked sensor rods in this embodiment. Rather, SS pins are daisy chained. Connector 450 in this embodiment is connected to the SS In pin of the stacked sensor (or sensor bus head) above it.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A modular sensor system, comprising:
   a sensor bus head located at a top end of the modular sensor system, the sensor bus head comprising at least one sensor bus head connector;
   a sensor bus terminus located at a bottom end of the modular sensor system, the sensor bus terminus comprising at least one sensor bus terminus connector; and
   at least one sensor rod connected between and in communication with the sensor bus head and the sensor bus terminus, the at least one sensor rod comprising a first sensor rod comprising at least one first top end connector in communication with the at least one sensor bus head connector via a first releasable pin connection, and at least one first bottom end connector in communication with the at least one sensor bus terminus connector via a second releasable pin connection,
   wherein the sensor bus head, sensor bus terminus, and the at least one sensor rod are configured to mechanically couple together in a stacked arrangement via the first and second releasable pin connections to enable hot-swapping of the at least one sensor rod,
   wherein the sensor bus terminus is configured to provide electrical loading to identify a terminal end of the modular sensor system; and
   wherein the at least one sensor rod comprising the first sensor rod is configured to determine environmental parameters of soil, water, or both, at its respective depth, and send data regarding the environmental parameters to the sensor bus head at the top end of the modular sensor system.

2. The modular sensor system of claim 1, wherein the at least one sensor rod is configured to determine chemical composition of soil and/or water, measure pressure, temperature, and/or moisture, or any combination thereof, at different depths.

3. The modular sensor system of claim 1, wherein the sensor bus head comprises a power and control interface.

4. The modular sensor system of claim 3, wherein the power and control interface comprises a solar panel, controls, and a display.

5. The modular sensor system of claim 1, wherein the sensor bus head comprises an antenna and circuitry that transmit analysis data to one or more other modular sensor systems, a central server via a cellular network, a local area network (LAN), a wide area network (WAN), a satellite communications network, or any combination thereof.

6. The modular sensor system of claim 1, wherein the at least one sensor rod is configured to communicate its depth to the sensor bus head.

7. The modular sensor system of claim 1, wherein
   the at least one sensor bus head connector, the at least one sensor bus terminus connector, the at least one first top end connector, and the at least one bottom end connector each comprises waterproof connectors comprising a power pin, a ground pin, a data pin, a clock pin, and a sensor select pin, wherein
   the power pin provides a supply voltage when communicating with the at least one sensor rod, the ground pin provides a reference ground for the sensor bus head, the sensor bus terminus, and the at least one sensor rod, the data pin facilitates bidirectional communication between the at least one sensor rod and the sensor bus head, the clock pin is shared by all of the at least one sensor rods and is controlled by the sensor bus head, and the sensor select pin is daisy chained and selects a current sensor rod of the at least one sensor rod that the sensor bus head is communicating with.

8. The modular sensor system of claim 1, wherein the power and control interface comprises a solar panel, controls, and a display.

9. The modular sensor system of claim 1, wherein the at least one sensor rod further comprises a second sensor rod comprising at least one second top end connector and at least one second bottom end connector, the second sensor rod positioned between and in communication with the sensor bus head and the sensor bus terminus, the second sensor rod configured to directly connect with the first sensor rod at the at least one first top end connector or the at least one first bottom end connector.

10. The modular sensor system of claim 1, wherein the sensor bus head defines a first most-terminal end of the modular sensor system, and the sensor bus terminus defines a second most-terminal end of the modular sensor system that is opposite the first most-terminal end, the sensor bus terminus comprising a penetrating tip opposite the at least one sensor bus terminus connector.

11. A modular sensor system, comprising:
a sensor bus head configured to be located at a top end of the modular sensor system, the sensor bus head comprising at least one sensor bus head connector, and a power and control interface configured to enable a user to select a function of the modular sensor system;
a sensor bus terminus configured to be located at a bottom end of the modular sensor system, the sensor bus terminus comprising at least one sensor bus terminus connector; and
at least one sensor rod configured to be connected between and in communication with the sensor bus head and the sensor bus terminus, the at least one sensor rod comprising a first sensor rod comprising at least one first top end connector in communication with the at least one sensor bus head via a first releasable pin connection, and at least one first bottom end connector in communication with the at least one sensor bus terminus connector via a second releasable pin connection, wherein the sensor bus head, sensor bus terminus, and the at least one sensor rod are configured to mechanically couple together in a stacked arrangement via the first and second releasable pin connections to enable hot-swapping of the at least one sensor rod, wherein the sensor bus terminus is configured to provide electrical loading to identify a terminal end of the modular sensor system; and wherein the at least one sensor rod comprising the first sensor rod is configured to determine environmental parameters of soil, water, or both, at its respective depth, and send data regarding the environmental parameters to the sensor bus head at the top end of the modular sensor system.

12. The modular sensor system of claim 11, wherein
the at least one sensor rod is configured to determine chemical composition of soil and/or water, measure pressure, temperature, and/or moisture, or any combination thereof, at different depths.

13. The modular sensor system of claim 11, wherein the at least one sensor rod is configured to communicate its depth to the sensor bus head.

14. The modular sensor system of claim 11, wherein
wherein the at least one sensor bus head connector, the at least one sensor bus terminus connector, the at least one first top end connector, and the at least one first bottom end connector each comprises a power pin, a ground pin, a data pin, a clock pin, and a sensor select pin, wherein the power pin is configured to provide a supply voltage when communicating with the at least one sensor rod, the ground pin is configured to provide a reference ground for the sensor bus head, the sensor bus terminus, and the at least one sensor rod, the data pin is configured to facilitate bidirectional communication between the at least one sensor rod and the sensor bus head, the clock pin is shared by all of the at least one sensor rods and is configured to be controlled by the sensor bus head, and the sensor select pin is daisy chained and is configured to select a current sensor rod of the at least one sensor rod that the sensor bus head is communicating with.

* * * * *